United States Patent [19]

Choyce

[11] 4,277,851

[45] Jul. 14, 1981

[54] INTRAOCULAR ANTERIOR CHAMBER IMPLANTS

[76] Inventor: David P. Choyce, 9 Drake Rd., Westcliff-on-Sea, Essex, England, SSO 8LR

[21] Appl. No.: 100,120

[22] Filed: Dec. 4, 1979

Related U.S. Application Data

[63] Continuation-in-part of Ser. No. 907,595, May 19, 1978, abandoned.

[30] Foreign Application Priority Data

Dec. 22, 1977 [GB] United Kingdom ............... 53425/77

[51] Int. Cl.³ .......................... A61F 1/16; A61F 1/24
[52] U.S. Cl. ......................................................... 3/13
[58] Field of Search ......................................... 3/13, 1

[56] References Cited

U.S. PATENT DOCUMENTS 4,092,743  6/1978  Kelman ..................................... 3/13

FOREIGN PATENT DOCUMENTS 959314  3/1957  Fed. Rep. of Germany ................ 3/13

OTHER PUBLICATIONS

The Mark VI, Mark VII and Mark VIII Choyce Anterior Chamber Implants, proceedings of The Royal Society of Medicine, vol. 58, Sep. 1965, pp. 729–731.
A Lens For All Seasons (book) by Jerald L. Tennant, M.D., Aug. 1976, pp. 13–21.
"Experience with 12 Cases of Intra-Ocular Anterior Chamber Implants for Aphakia" by J. Boberg-Ans, British Journal of Ophthalmology, vol. 45, No. 1, Jan. 1961, pp. 37–43.

Primary Examiner—Ronald L. Frinks
Attorney, Agent, or Firm—Lewis Messulam

[57] ABSTRACT

An intraocular anterior chamber implant which can be used successfully in widths of 5 mm or less comprises an optic and a haptic which consists of a pair of bridging members each of which joins one of diametrically opposed edges of the optic to a support member. The support members each have a scalloped edge, whereby a pair of co-planar "U" shaped support surfaces is provided, and each bridging member has scalloped side edges to reduce its width relative to the optic.

1 Claim, 5 Drawing Figures

INTRAOCULAR ANTERIOR CHAMBER IMPLANTS

RELATED APPLICATION

The present application is a continuation in part of my copending application Ser. No. 907,595, filed on May 19, 1978, now abandoned.

BACKGROUND OF THE INVENTION

This invention relates to an intraocular anterior chamber implant.

Intraocular anterior chamber implants have been developed over the last twenty five years and are primarily used for the correction of aphakia.

Such intraocular implants include an optic portion which acts as a lens so as to perform the function of the lens of the eye which has been removed and a haptic portion by means of which the implant is held in position.

It was found some years ago that a very desirable material for such an intraocular anterior chamber implant is polymethylmethacrylate usually known as PMMA and sold in clinical quality under the Trade Mark "Perspex CQ". It has been found that an implant made of this material which is properly held in position can be tolerated by the eye.

I proposed some years ago the use of an intraocular anterior chamber implant comprising an optic integral with a haptic which includes two pairs of feet projecting in opposite directions away from the optic. Such an intraocular anterior chamber implant is illustrated in FIGS. 1 and 2 in which the optic is indicated at 1 and is biconvex. The haptic consists of two pairs of feet 2 and 3 projecting from opposite sides of the optic from a part frusto-conical ledge 4. Each foot is shown with a circular hole 5 which may be omitted.

While implants of the type illustrated in FIGS. 1 and 2 have met with considerable success, the need remained for further improvement in the design. In particular such implants have been used successfully only in widths of 6 or 7 mm, requiring incisions of 7 or 8 mm respectively for their insertion. It is often highly desirable to make use of a narrower implant, e.g. one which is only 5 mm or even 4 mm wide. An obvious advantage of using a narrower implant is the reduction in the incision needed for its insertion to 6 mm or even 5 mm. A narrow implant is desirable when the eye into which it is to be inserted is relatively small. Moreover a narrow implant is particularly desirable when it is to be inserted into an eye from which a cataract has been extracted. In such cases the secondary implantation is normally performed after the eye has recovered from the phacoemulsification or allied procedure used for the cataract extraction.

Despite the need for narrower implants, no design heretofore known has been suitable for providing an implant having a width of 5 mm or less which is stable in use, i.e. has no tendency to move after it has been inserted in position and does not damage or iritate tissues and surfaces with which it comes into contact. In particular attempts to merely scale down the implant design of FIGS. 1 and 2 to produce an implant 5 mm or less wide, as well as attempts to file down a 6 mm wide implant to produce the desired narrower one have not been found to yield a stable implant.

OBJECT OF THE INVENTION

It is an object of the invention to provide an improved intraocular anterior chamber implant which is stable in use even when constructed in widths of 5 mm of less.

SUMMARY OF THE INVENTION

The present invention provides an intraocular anterior chamber implant consisting of an integrally formed elongate structure which comprises:

a central lens which does not exceed 5 mm in diameter;

first and second support members of substantially the same width as the lens diameter, situated on diametrically opposed sides of the lens and spaced therefrom, each support member having a flat support surface which, in use, rests on the iris of an eye into which the implant is inserted; and first and second bridging members each of which extends between and interconnects an edge of a respective support member and an edge of the lens, the bridging members being shaped and dimensioned such that said support surfaces lie in a common plane spaced from the lens;

wherein each support member has a concave edge remote from the lens such that the support surface thereof is a generally 'U' shaped surface with the members of said U constituting feet and the trough of said U constituting a connecting portion which connects the feet to one another and to the respective bridging member, and wherein each bridging member has concave side edges so that at least a portion of said bridging member is narrower than the lens diameter.

The width of the implant is preferably limited to the diameter of the optic, i.e. the central lens, which is preferably between 4 mm and 5 mm. The haptic of this implant, consisting of the bridging members and the support members, has concave end-edges and concave side-edges. The concavity, or scalloping, of the end edges aids in reducing the size and weight of the implant. Such scalloping must not however be so deep as to unduly reduce the available surface area of the support surfaces, since any reduction of the latter increases the pressure exerted thereby on the iris. For this reason the scalloping of the edge of a support member must not extend as far as opposite edge of that support member, but only part of the way to leave a 'U' shaped support surface.

The concavity, or scalloping, of the edges of the bridging members reduces the intraocular bulk of the implant, which is desirable in that it reduces the obstruction to free circulation of the aqueous liquid in the anterior chamber. This has the effect that post operative swelling or oedema of the iris becomes less serious if it does occur and is therefore less likely to lead to post operative prolapse of the iris in front of the implant.

It may be desirable for the optic to be plano-convex with the planar surface anterior because it is thought that this form best matches the spherical aberration of the natural lens of the eye and moves the refracting surface as far back as possible. However, a bi-convex optic as shown in FIG. 1 is alternatively usable as would be a plano-convex optic with its planar surface posterior.

In a preferred embodiment of the invention each of the bridging members is in the form of a part frusto-conical ledge, and includes an aperture which is large enough to receive a suture while at the same time permitting fluid flow between opposite faces of the haptic. The apertures are preferably of the order of 1 mm in diameter.

DETAILED DESCRIPTION OF THE EMBODIMENT

Figure 1:
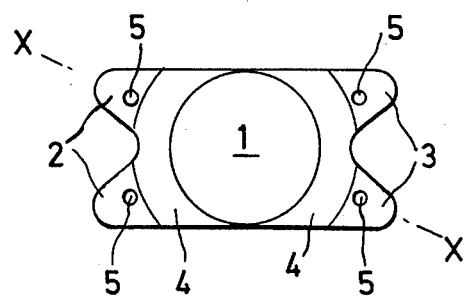
FIGS. 1 and 2 are, respectively, a plan view and a section on line X—X of a known anterior chamber implant.
Figure 2:
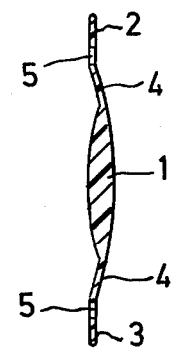
Figures 3, 4, 5:
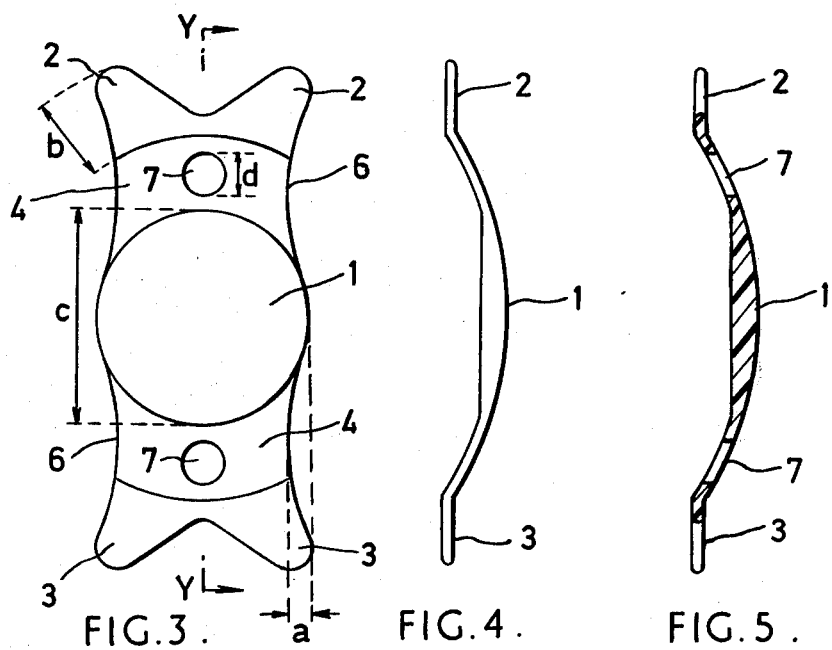
FIGS. 3 and 4 are, respectively, a plan view and a side view of an anterior chamber implant according to a preferred feature of the invention.
FIG. 5 is a cross-section along the line Y—Y of FIG. 3.

In FIGS. 3 to 5 the numerals used are, wherever possible, the same as those use for corresponding parts in FIGS. 1 and 2. Accordingly only the details of the preferred embodiment which differ from those of the known implant of FIGS. 1 and 2 will be described below.

In the embodiment illustrated in FIGS. 3 to 5, the optic 1 is a plano-convex lens having a diameter "c" of 5 mm. The haptic of this embodiment includes bridging members 4 which are in the form of part frusto-conical ledges. Each of the bridging members includes a central aperture 7 having a diameter "d" of 1.0 mm. The side edges 6 of the bridging members are scalloped as shown, and the depth "a" of the scalloping, which is chosen in accordance with the length and width of the implant, should not exceed 0.5 mm.

The apertures 7 serve several useful and important functions in the implant of the invention. The first of these is that they permit fluid flow within the anterior chamber, a function which is also served by the scalloping of the side edges 6. Moreover both the scalloping of the side edges 6 and the apertures 7 serve to reduce the weight of the implant, which in turn renders it less likely to move within the eye. It will of course be appreciated that it is important that the position of the implant remain fixed within the eye.

The apertures 7 also facilitate positioning of the implant since an instrument can be placed into the apertures to rotate the implant when it is inserted into the eye. Yet another function of these apertures is that of providing additional fixation of the implant, in that a stitch or suture can be passed through the aperture and then brought out through the sclera. The diameter of the aperture ensures that fluid circulation can take place therethrough despite the presence of the suture therein.

The support members of this embodiment will be seen to consist mainly, but not entirely, of the feet 2 and 3. Unlike the feet in the prior known embodiment, the feet in the implant of the invention are not individually attached to the respective bridging member, but rather terminate at a linking portion of the support member which connects each pair of feet to one another and the bridging member. The linking portion of the support member together with its respective pair of feet define a generally "U" shaped support surface. To ensure this shape the scalloping between the feet must be less than the dimension "b" shown in FIG. 3. The dimension "b" of the support member should be approximately 2 mm regardless of the overall length of the implant, and preferably should be between 1.75 and 2.25 mm. The correct choice of the shape and dimensions of the support surfaces is essential to the success of the invention in that it minimizes the pressure which can be exerted on the iris.

The ends of the feet are rounded or radiused as is the concave region between the feet in each pair. The radius of both curves is preferably 0.50 mm. The edges of the whole implant are also rounded when viewed in section to avoid traumatising any delicate tissues with which they may come into contact.

It is still not decided whether a 4 mm diameter optic or a 5 mm diameter optic is superior.

It is intended that the 5 mm width will be used in the larger eye, i.e. when the implant length required is 12.5 mm or longer and that the 4 mm width version should be used when the implant length is 12.0 mm or less. The length of the implant can vary from 10 mm to 14 mm in 0.5 mm steps.

The reduction in the dimensions of the optic has been found to be theoretically desirable for optical reasons, in that for any given curvatures of the front and rear faces of a lens, the maximum thickness of the lens decreases as the lens width is decreased. Thus the use of a narrower optic results in an increased clearance between the rear surface of the optic and the pupil, thereby enabling improved circulation within the anterior chamber.

The optical powers may be similar to those previously used, i.e. from the spectacle equivalent of +7 dioptre steps (14D power in aqueous) to the spectacle equivalent of +15 dioptre steps (24D power in aqueous) in 2 dioptre steps. It is desirable that the lens be manufactured from clinical quality polymethylmethacrylate (Perspex CQ) by machining on a lathe and subsequent hand polishing, although other plastics, or glass or other transparent material may be suitable.

It will be understood that the invention has been specifically described with reference to preferred embodiments thereof, and various modifications may be made to the details of those embodiments without departing from the scope of the invention, which is defined by the appended claims.

I claim:

1. An intraocular anterior chamber implant consisting of an integrally formed elongate structure which comprises:

a central lens which does not exceed 5 mm in diameter;

first and second support members of substantially the same width as the lens diameter, situated on diametrically opposed sides of the lens and spaced therefrom, each support member having a flat support surface which, in use, rests on the iris of an eye into which the implant is inserted; and first and second bridging members each of which extends between and interconnects an edge of a respective support member and an edge of the lens, the bridging members being shaped and dimensioned such that said support surfaces lie in a common plane spaced from the lens;

wherein each support member has a concave edge remote from the lens such that the support surface thereof is a generally 'U' shaped surface with the members of said U constituting feet and the trough of said U constituting a connecting portion which connects the feet to one another and to the respective bridging member, wherein each bridging member has concave side edges so that at least a portion of said bridging member is narrower than the lens diameter, and wherein each bridging member has an aperture between the said edges thereof, said aperture being of at least approximately 1 mm diameter, whereby in use fluid flow can take place through said aperture despite the presence of surgical thread therein.

* * * * *